United States Patent
Bonnette et al.

(10) Patent No.: US 7,220,243 B2
(45) Date of Patent: *May 22, 2007

(54) GAS INFLATION/EVACUATION SYSTEM AND SEALING SYSTEM INCORPORATING A COMPRESSION SEALING MECHANISM FOR GUIDEWIRE ASSEMBLY HAVING OCCLUSIVE DEVICE

(75) Inventors: Michael J. Bonnette, Minneapolis, MN (US); Eric J. Thor, Arden Hills, MN (US); Richard R. Prather, St. Michael, MN (US)

(73) Assignee: Possis Medical, Inc., Minneapolis, MN (US)

( * ) Notice: Subject to any disclaimer, the term of this patent is extended or adjusted under 35 U.S.C. 154(b) by 139 days.

This patent is subject to a terminal disclaimer.

(21) Appl. No.: 10/838,464

(22) Filed: May 4, 2004

(65) Prior Publication Data

US 2005/0020998 A1 Jan. 27, 2005

Related U.S. Application Data

(63) Continuation-in-part of application No. 10/012,903, filed on Nov. 6, 2001, now Pat. No. 6,932,828, and a continuation-in-part of application No. 10/012,891, filed on Nov. 6, 2001, and a continuation-in-part of application No. 10/007,788, filed on Nov. 6, 2001, now Pat. No. 6,942,678.

(51) Int. Cl.
*A61M 29/00* (2006.01)

(52) U.S. Cl. .................. 604/99.01; 606/191; 604/250
(58) Field of Classification Search ............ 604/96.01, 604/97.01, 97.02, 98.01, 99.01–99.04, 103, 604/103.03, 250; 606/191–192
See application file for complete search history.

(56) References Cited

U.S. PATENT DOCUMENTS

| | | | | |
|---|---|---|---|---|
| 5,795,325 | A * | 8/1998 | Valley et al. ............... | 604/509 |
| 6,932,828 | B2 * | 8/2005 | Bonnette et al. ............ | 606/194 |
| 7,004,914 | B2 * | 2/2006 | Eberhart et al. ............ | 600/585 |
| 7,169,161 | B2 * | 1/2007 | Bonnette et al. ............ | 606/191 |

* cited by examiner

*Primary Examiner*—Kevin C. Sirmons
*Assistant Examiner*—Andrew Gilbert
(74) *Attorney, Agent, or Firm*—Hugh D. Jaeger, Esq.

(57) ABSTRACT

A gas inflation/evacuation system and sealing system for use with occlusive devices in vascular procedures. The gas inflation/evacuation system is removably connectable via the sealing system to a proximal portion of a guidewire assembly having a guidewire that defines a lumen and includes a first syringe system for evacuating the lumen and a second syringe system for introducing a biocompatible gas into the lumen to inflate an occlusive balloon that is in fluid communication with the lumen a plurality of times. The sealing system selectively seals the proximal portion of the guidewire and includes a crimping mechanism and a compression sealing mechanism having a resilient seal for sealing around the proximal portion of the guidewire when it is passed therethrough.

15 Claims, 16 Drawing Sheets

GAS INFLATION/EVACUATION SYSTEM AND SEALING SYSTEM INCORPORATING A COMPRESSION SEALING MECHANISM FOR GUIDEWIRE ASSEMBLY HAVING OCCLUSIVE DEVICE

CROSS REFERENCES TO RELATED APPLICATIONS

This application is a continuation-in-part of U.S. patent application Ser. No. 10/012,903, filed Nov. 6, 2001, entitled "Guidewire Occlusion System Utilizing Repeatably Inflatable Gas-Filled Occlusive Device," now U.S. Pat. No. 6,932,828, and U.S. patent application Ser. No. 10/012,891, filed Nov. 6, 2001, entitled "Guidewire Assembly Having Occlusive Device and Repeatably Crimpable Proximal End," and U.S. patent application Ser. No. 10/007,788, filed Nov. 6, 2001, entitled "Gas Inflation/Evacuation System and Sealing System for Guidewire Assembly Having Occlusive Device," now U.S. Pat. No. 6,942,678, all of which are hereby incorporated herein by reference.

BACKGROUND OF THE INVENTION

1. Field of the Invention

The present invention relates generally to the field of vascular medical devices. More specifically, the present invention relates to a gas inflation/evacuation system and sealing system incorporating a compression sealing mechanism and a crimping mechanism for selectively and repeatedly inflating an occlusive balloon and for sealing and crimping an extended sealable section at the proximal end of a guidewire during an occlusion procedure.

2. Description of the Prior Art

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of non-surgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320,604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically-expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long, straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard non-surgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S.

Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520,645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons as well as most guidewire occlusive balloons utilize a liquid fluid such as saline or saline mixed with a radiopaque marker for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high-pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternate embodiments in U.S. Pat. No. 6,217,567. The only suggestion for how the guidewire of the alternate embodiment is sealed is a valve type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid filled occlusive balloons can remain in place too long and take too long to deflate, increasing the risk of damages downstream of the occlusion. Occlusive filters are designed to address this problem, but suffer from blockage problems and can be complicated to deploy and retrieve and may allow small embolic particles to migrate downstream. Existing gas-filled occlusive balloons solve some of the problems of liquid filled occlusive balloons, but typically have utilized complicated valve and connection arrangements. It would be desirable to provide for an occlusive device that was effective, simple, quick to deploy and deflate, and that could overcome the limitations of the existing approaches.

Some of these problems have been previously addressed in three commonly owned and assigned co-pending applications, which are hereby incorporated by reference herein: "Guidewire Occlusion System Utilizing Repeatably Inflatable Gas-Filled Occlusive Device," application Ser. No. 10/012,903, filed Nov. 6, 2001; "Guidewire Assembly Having Occlusive Device and Repeatably Crimpable Proximal End," application Ser. No. 10/012,891, filed Nov. 6, 2001; and "Gas Inflation/Evacuation System and Sealing System for Guidewire Assembly Having Occlusive Device," application Ser. No. 10/007,788, filed Nov. 6, 2001.

SUMMARY OF THE INVENTION

Disclosed herein is a gas inflation/evacuation system and sealing system that incorporates a compression sealing mechanism that seals around multiple elongated elements that puncture a seal of the compression sealing mechanism.

The compression sealing mechanism can seal around three or more wires, tubes, or other elongated elements so that the compression sealing mechanism can be used a plurality of times without replacing parts of the compression sealing mechanism. The compression sealing mechanism effectively seals around three or more wires, tubes, or other elongated elements and is superior to other sealing mechanisms that can seal around only two wires, tubes, or other elongated elements.

The compression sealing mechanism may be used to seal around a guidewire of a guidewire assembly that cooperates with a gas inflation/evacuation system that is proximal to the seal. The proximal portion of the guidewire may be cut distal to the seal, leaving a portion of the proximal portion of the guidewire in the seal. The intact proximal portion of the guidewire may subsequently be reinserted into the seal to re-engage the gas inflation/evacuation system. Therefore, the seal must effectively seal around a plurality of guidewire portions. The compression sealing mechanism is readily adaptable to systems as described in U.S. patent applications Ser. Nos. 10/012,903; 10/012,891 and 10/007,788. As disclosed in those patent applications, a gas inflation/evacuation system is combined with a sealing system that includes a crimping mechanism and a sealing mechanism, and these systems are removably connectable to a guidewire assembly having an occlusive device located near its distal end. The gas inflation/evacuation system is removably connectable to the proximal end of the guidewire assembly and comprises an evacuation system which includes means for evacuating the guidewire assembly and an inflation system which includes means for introducing a gas under pressure into the guidewire assembly to inflate the occlusive device, such as an occlusive balloon, a plurality of times.

An embodiment set forth herein is a gas inflation/evacuation system removably connectable to a proximal portion of a guidewire assembly having a guidewire that defines a lumen. The gas inflation/evacuation system may include a first syringe system that includes an evacuation syringe for selectively evacuating the lumen, and a second syringe system that includes an inflation syringe or syringes for selectively introducing a biocompatible gas into the lumen to inflate an occlusive balloon in fluid communication with the lumen and located proximate a distal end of the guidewire assembly. Further, a sealing system may be removably connected to the proximal portion of the guidewire assembly and the lumen, the sealing system including a crimping mechanism and a compression sealing mechanism.

The compression sealing mechanism includes a resilient seal for receiving and sealing around a proximal portion of a guidewire, and a compressing apparatus that compresses at least a portion of the resilient seal. The compressive force is transmitted into the seal and compresses the seal around tubes, wires, or other elongated elements that pass through the seal. A plurality of guidewires may penetrate the seal, e.g., between 2 and 6, or at least two or three. The compression sealing system operates automatically; that is, when the resilient seal is penetrated by a tube, wire, or other elongated element inserted therethrough, the compressed resilient seal automatically causes sealing around the element that has penetrated it.

An example of apparatus for compressing the seal is an assembly of axially related backing or retaining members that include sealing surfaces that contact the seal. A compressive force is applied to the seal via the sealing surfaces. Examples of backing or retaining members are threaded members such as nuts, caps, screw followers, and sealing glands. Further examples of backing or retaining members for applying a compressive force include springs, tensioned parts, and biased members. For example, a disc-shaped seal may be compressed between two planar sealing surfaces, e.g., one planar sealing surface being a sealing face on a sealing cap and the other planar sealing surface being a sealing seat in a sealing gland. A specific type of seal can be one made of a resilient material, e.g., a polymer, for example, an elastomeric polymer. Seals of various geometries are contemplated, e.g., disc-shaped, spherical, and polygonal. Examples of the thickness of a seal are from about 0.030 inch to about 0.200 inch.

An advantage of the present invention is that the occlusive device can be repeatably inflated and deflated a plurality of times during a vascular procedure in between which the proximal end of the guidewire is free of mechanical connections and obstructions and, therefore, the guidewire can function as a conventional exchange guidewire for one or more over-the-wire catheters. Alternatively, the guidewire can be shorter in length for use with rapid exchange catheter systems. Unlike operation of existing liquid filled occlusive devices, the present invention enables repeated and quick inflation and deflation which allows an operator to deploy the gas-filled occlusive device numerous times during a procedure for shorter periods of time, thereby reducing the risk of potential damage to downstream tissue. Unlike operation of other gas-filled occlusive devices, the simplicity of the present invention permits the guidewire to be used as a conventional exchange guidewire. There are no complicated mechanical arrangements or valve systems internal to the guidewire that increase the cost, complexity, and potential for failure of the system.

In a preferred embodiment, the extended sealable section is an extended crimpable section and the sealing system includes a crimping mechanism as well as the compression sealing mechanism. The extended crimpable section has a sufficient length to permit a plurality of crimps and cuts along the extended crimpable section and preferably has an outer diameter that is smaller than the outer diameter of the main body portion of the guidewire. The crimping mechanism is used to crimp the extended crimpable section of the guidewire to seal the guidewire a plurality of times. Preferably, the gas inflation/evacuation system and the crimping mechanism and the compression sealing mechanism of the sealing system constitute a handheld apparatus. Alternatively, the sealing system composed of the crimping mechanism and the compression sealing mechanism may be a handheld unit completely separate from the gas inflation/evacuation system. Each time a deflation of the occlusive device is desired in order to reestablish blood flow to the vessel downstream of the occlusive device, the extended crimpable section is cut distal to the location of the last crimp so as to quickly deflate the occlusive device. Preferably, the extended crimpable section of the guidewire is dimensioned and the crimping mechanism is arranged such that an effective outer diameter of the extended crimpable section at the location of a seal is no greater than the outer diameter of the main body portion of the guidewire when the extended crimpable section is sealed.

In a preferred embodiment, the inflation system of the gas inflation/evacuation system includes a plurality of individually actuatable syringes each containing a sufficient volume of biocompatible gas for a single inflation of the occlusive device so as to minimize the volume of biocompatible gas in the gas inflation/evacuation system in the event of a leak.

One significant aspect and feature of the present invention is a gas inflation/evacuation system and sealing system for a guidewire assembly having an occlusive device wherein the sealing system includes a crimping mechanism and a compression sealing mechanism.

Another significant aspect and feature of the present invention is a resilient seal that automatically and effectively seals around three or more elongated elements inserted therethrough.

Still another significant aspect and feature of the present invention is compression apparatus which operates to compress a resilient seal into sealing relationship with elongated elements passing therethrough and by which the degree of compression of the resilient seal can be varied.

Yet another significant aspect and feature of the present invention is a compression sealing mechanism which includes an imperforate seal that seals around elements pushed therethrough.

Having thus described embodiments of the present invention and enumerated significant aspects and features thereof, it is the principal object of the present invention to provide a gas inflation/evacuation system and sealing system incorporating a compression sealing mechanism for a guidewire assembly having an occlusive device.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
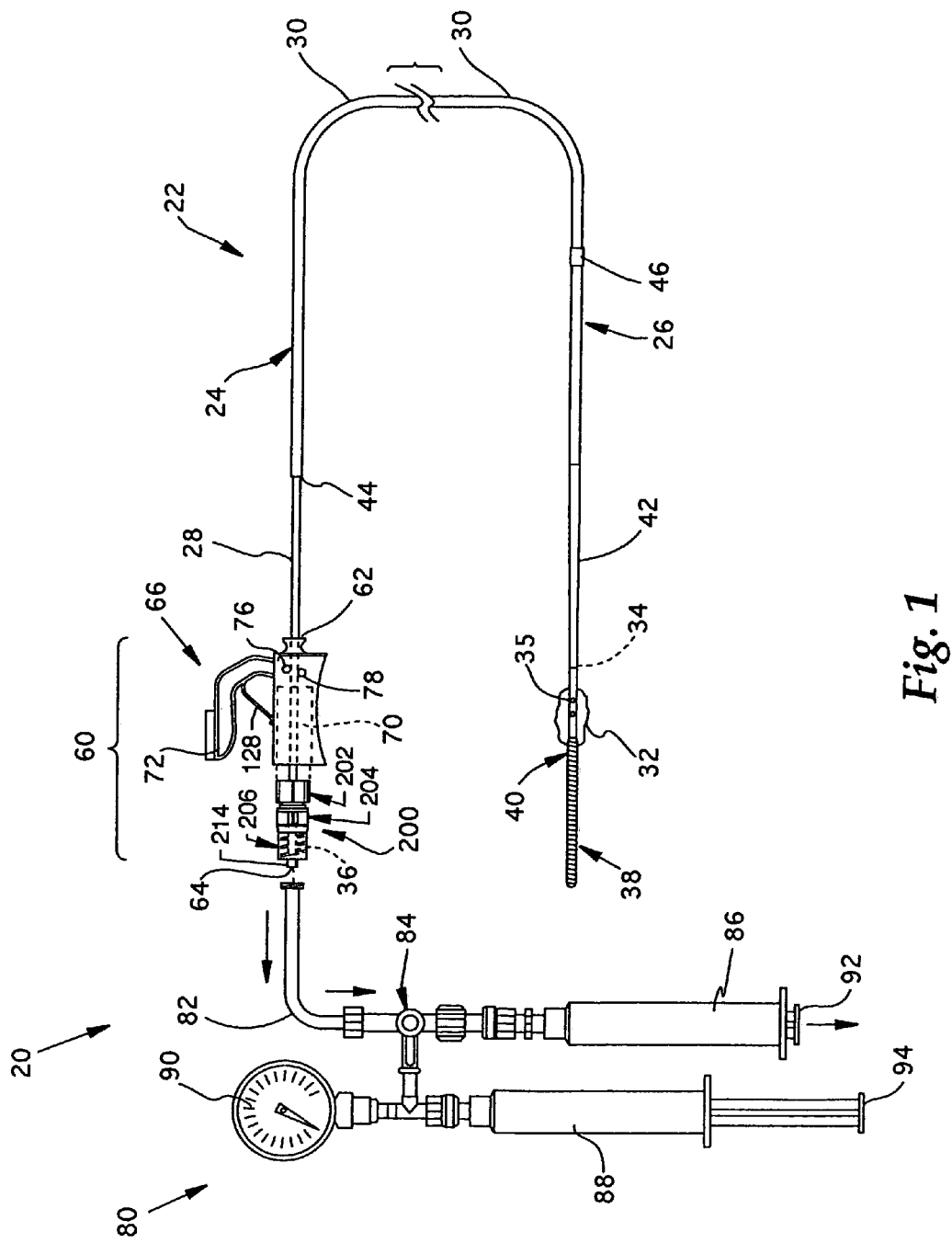
FIG. 1 is a schematic diagram of a guidewire occlusion system operating in an evacuation mode and incorporating a gas inflation/evacuation system and sealing system in accordance with the present invention.
Figure 2:
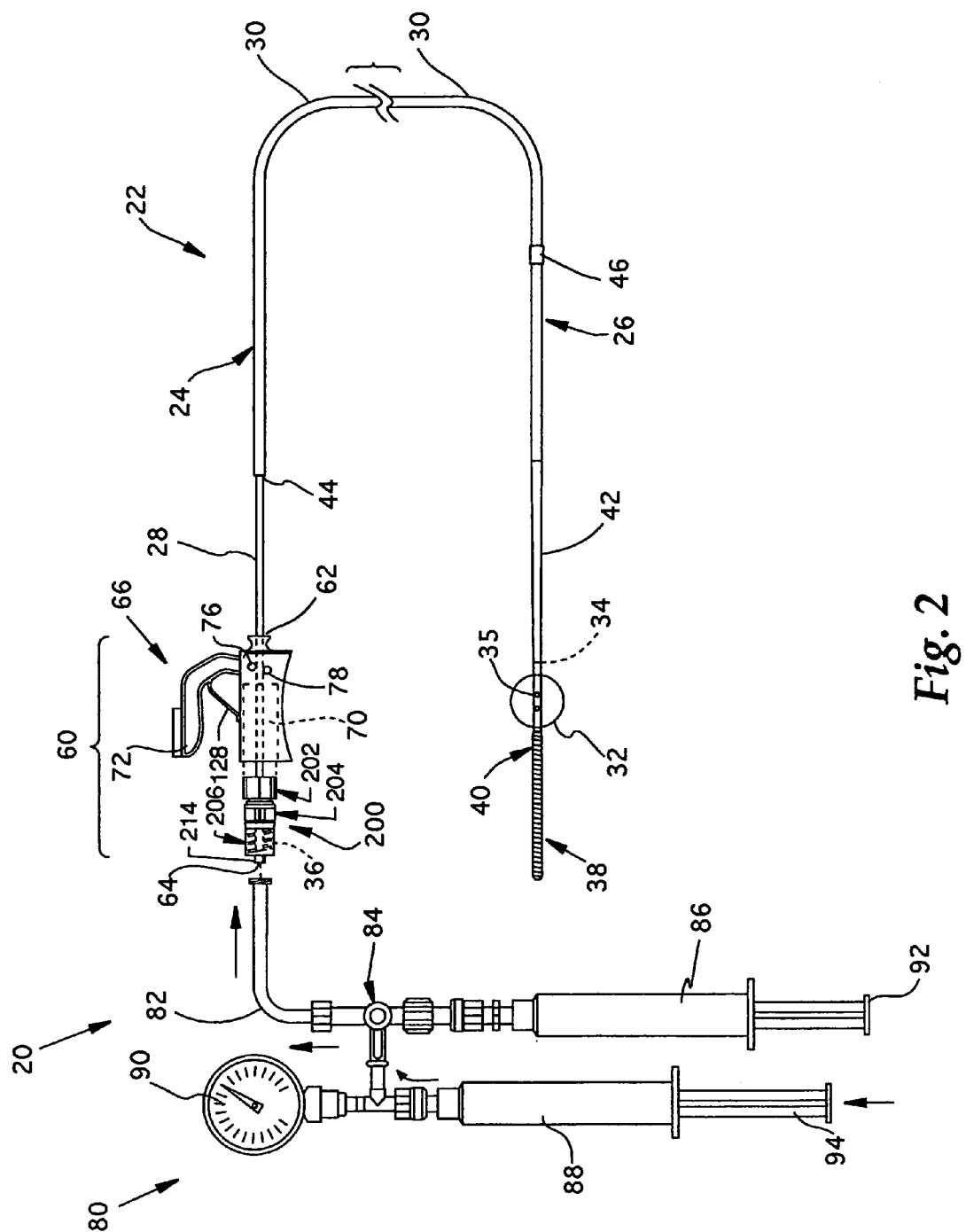
FIG. 2 is a schematic diagram of the guidewire occlusion system shown in FIG. 1 operating in an inflation mode.

Referring now to FIGS. 1 and 2, the overall structure and operation of a guidewire occlusion system 20 incorporating the present invention will be described. The guidewire occlusion system 20 includes a guidewire assembly 22, a sealing system 60, and a gas inflation/evacuation system 80. The preferred embodiments of the overall guidewire occlusion system 20 are described in further detail in the previously identified co-pending applications entitled "Guidewire Occlusion System Utilizing Repeatably Inflatable Gas-Filled Occlusive Device", "Guidewire Assembly Having Occlusive Device and Repeatably Crimpable Proximal End, ", and "Gas Inflation/Evacuation System and Sealing system for Guidewire Assembly Having Occlusive Device".

Guidewire assembly 22 includes a guidewire 24, an occlusive device such as an occlusive balloon 32, and, optionally, a flexible tip 38. The guidewire 24 is tubular and comprises an extended sealable section 28, a main body portion 30, and a distal portion 26. Extended sealable section 28 is generally a separate piece which extends from the proximal end 36 of the guidewire 24 to the main body portion 30 to which it is joined, preferably by a laser weld 44. The distal portion 26 also is generally a separate piece which is joined to the main body portion 30, preferably by an Ni—Ti or stainless steel sleeve 46, and extends distally from the main body portion 30 to the distal end 40 of the guidewire 24. As used in the present invention, the terms proximal and distal will be used with reference to an operator, such that a distal portion of the guidewire 24, for example, is the portion first inserted into a blood vessel, and the proximal portion remains exterior to the patient and is therefore closer to the operator. Preferably, the extended sealable section 28 is an extended crimpable section comprised of a tubular segment having an outer diameter smaller than an outer diameter of the main body portion 30 of guidewire 24. Although the diameter of the extended crimpable section could be any size consistent with effective use as a guidewire, it will be understood that the smaller diameter allows for less force to be used in sealing the extended crimpable section and provides a crimped seal that is not too large when crimped. The occlusive balloon 32 is located along the distal portion 26 of guidewire 24. The occlusive balloon 32 is fluidly connected via a lumen 34 to the proximal end 36 of guidewire 24, with channels or holes 35 allowing for fluid communication between lumen 34 and occlusive balloon 32. In a preferred embodiment, the flexible tip 38 is used and it is positioned at the distal end of the guidewire assembly 22. Preferably, distal portion 26 of guidewire 24 includes a tapered portion 42 to increase the flexibility and transition properties of the distal portion 26.

Preferably, sealing system 60 is implemented as part of a handheld apparatus that also includes gas inflation/evacuation system 80. Alternatively, sealing system 60 may be a handheld unit completely separate from the gas inflation/ evacuation system 80 (see FIGS. 3 and 4). Sealing system 60 includes a first aperture 62 into which the proximal end 36 of the guidewire 24 is insertable so as to operably position at least a portion of the extended sealable section 28 in relation to sealing system 60. Sealing system 60 further includes a second aperture 64 that is fluidly connectable to gas inflation/evacuation system 80 by a conduit 82. The sealing system 60 includes means for selectively sealing the extended sealable section 28 which in the preferred embodiment comprises a crimping mechanism 66 and a compression sealing mechanism 200. A passageway 70 is defined from first aperture 62 to second aperture 64 and extends through both crimping mechanism 66 and compression sealing mechanism 200. A portion of the extended sealable section 28 is inserted into first aperture 62 a sufficient distance to engage crimping mechanism 66 and compression sealing mechanism 200.

The gas inflation/evacuation system 80 is connected via conduit 82 to the second aperture 64 of the sealing system 60. The gas inflation/evacuation system 80 preferably includes a valve arrangement 84 that selectively couples one of an evacuation system which includes means for evacuating the guidewire assembly 22 and an inflation system which includes means for introducing a gas into the guidewire assembly 22 to the conduit 82. The evacuation system includes an evacuation syringe 86 having a plunger 92 which is used to evacuate the guidewire assembly 22, passageway 70, and conduit 82. The inflation system includes an inflation syringe 88 having a plunger 94 which contains a volume of a biocompatible gas sufficient to inflate the occlusive balloon 32 a plurality of times. Preferably, the biocompatible gas is carbon dioxide. Other biocompatible gasses that may be utilized with the present invention include oxygen, nitrogen, and nitrous oxide. Optionally, a pressure gauge 90 can be associated with the inflation syringe 88.

In a preferred embodiment, guidewire assembly 22 is constructed as described in further detail in the previously identified co-pending application Ser. No. 10/012,891 entitled "Guidewire Assembly Having Occlusive Device And Repeatably Crimpable Proximal End." The main body portion 30 is formed of a stainless steel hypotube having an outer diameter of 0.014 inch and an inner diameter of 0.007 inch. To accomplish passive deflation in the desired time of less than one minute when the extended sealable section 28 is cut, it is preferable that the main body portion 30 have an inner diameter of at least 0.002 inch. The extended sealable section 28 of guidewire 24 is comprised of a crimp tube also formed of stainless steel and having an outer diameter of 0.009 inch to 0.015 inch and an inner diameter of at least 0.002 inch and preferably about 0.005 inch. As mentioned before, the extended sealable section 28 is generally a separate piece secured to the main body portion 30 by a laser weld 44. Alternatively, the extended sealable section 28 may be formed by centerless grinding or reducing the outer diameter of a portion of the proximal portion of the main body portion 30 of guidewire 24. Still other embodiments may enable the extended sealable section to be a modified, treated or otherwise fabricated portion of the proximal portion of the main body portion 30 that is suitable for the particular sealing technique to be used.

The extended sealable section 28 can be made of any material that when deformed and severed retains that deformation so as to form an airtight seal. When crimped and severed, it is preferable that the extended sealable section 28 not present a sharp, rigid point that is capable of piercing a gloved hand. It has been found that so long as the preferred embodiment is not gripped within less than one inch of the proximal end of the extended sealable section 28, the severed proximal end of the extended sealable section 28 does not penetrate a standard surgical glove. In addition, the extended sealable section 28 must have sufficient strength in terms of high tensile and kink resistance to permit catheter devices to repeatedly pass over the extended sealable section 28.

The main body portion 30 is preferably secured to the distal portion 26 using a Ni—Ti or stainless steel sleeve 46 laser welded to the main body portion 30 and crimped to the distal portion 26. The distal portion 26 is preferably formed of a Ni—Ti alloy having an inner diameter of 0.0045 inch and an outer diameter that ranges from 0.014 inch to 0.0075 inch to form tapered portion 42, preferably formed by a centerless grinding process. The flexible tip 38 is a coiled tip attached to distal portion 26 distal to occlusive balloon 32, preferably by crimping. Alternatively, a sleeve could be welded to the flexible tip 38, and the tapered portion 42 could then be inserted into this sleeve and crimped.

Alternatively, any number of other alloys or polymer materials and attachment techniques could be used in the construction of the guidewire 24, provided the materials offer the flexibility and torque characteristics required for a guidewire and the attachment techniques are sufficiently strong enough and capable of making an airtight seal. These materials include, but are not limited to, Ni—Ti, 17-7 stainless steel, 304 stainless steel, cobalt superalloys, or other polymer, braided or alloy materials. The attachment techniques for constructing guidewire 24 include, but are not limited to, welding, mechanical fits, adhesives, sleeve arrangements, or any combination thereof.

The occlusive balloon 32 may be made of any number of polymer or rubber materials. Preferably, the occlusive balloon is preinflated to prestretch it so that expansion is more linear with pressure. Preferably, the pressure supplied by gas inflation/evacuation system 80 is designed to stay well within the elastic limit of the occlusive balloon 32. A two-layer occlusive balloon arrangement, adding gas and/or liquid between balloon layers, may be used in an alternate embodiment to increase visibility of the distal end 40 of the guidewire 24 under fluoroscopy.

Figure 3:
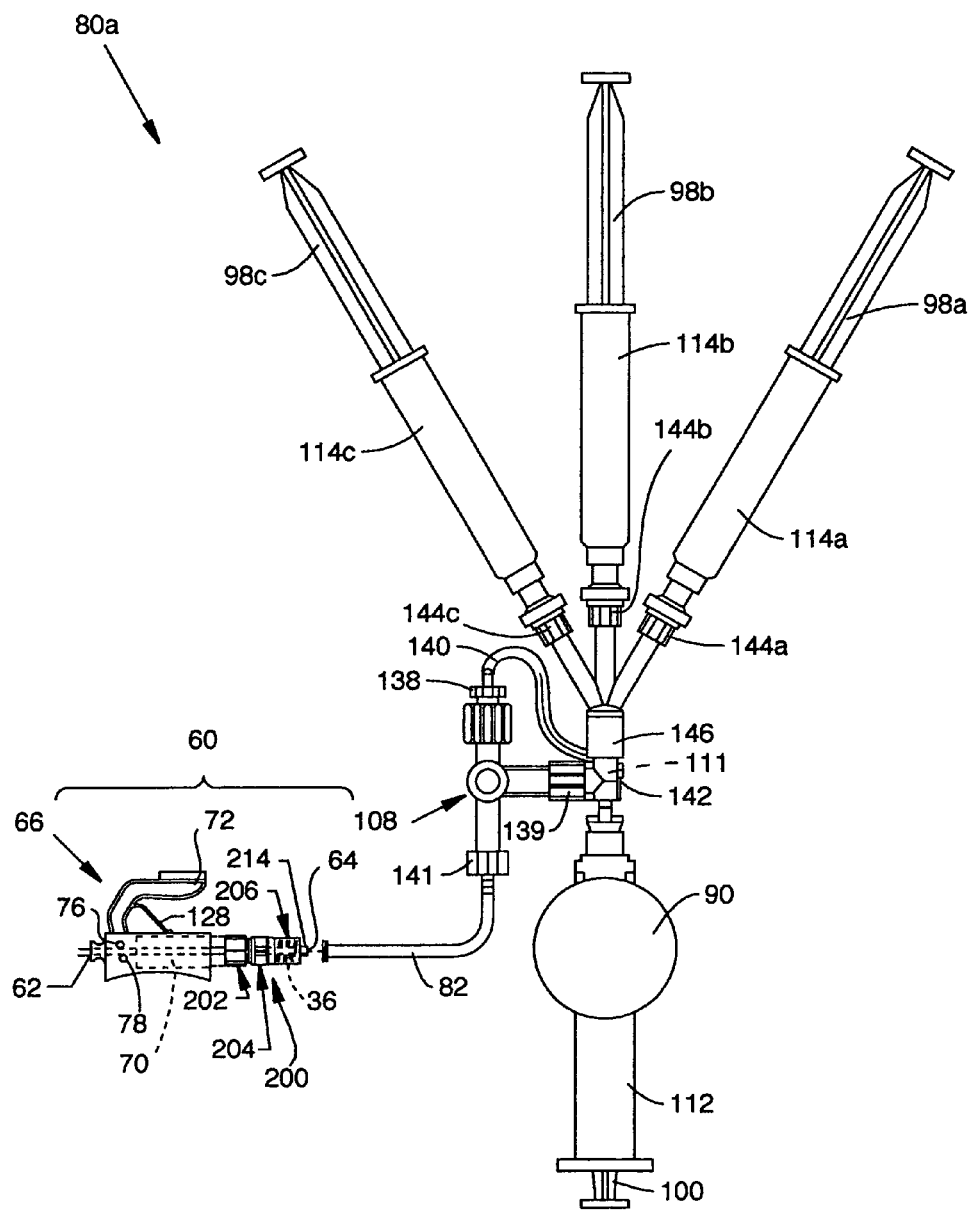
FIG. 3 is a top view of an alternate embodiment of a gas inflation/evacuation system and sealing system of the present invention.

FIG. 3 shows an alternate gas inflation/evacuation system 80*a* coupled to sealing system 60. A valve arrangement 108 has a coupling 141 connected to conduit 82 and a port 138 that is attached via a one-way check valve 111 and a hose 140 to an evacuation syringe 112 having an evacuation syringe plunger 100. Attached to an interconnect fitting 139 of the valve arrangement 108 is an inflation manifold 142. Inflation manifold 142 is connected to connector 146 and pressure gauge 90. Inflation manifold 142 has three check valves 144*a*, 144*b* and 144*c*. Check valves 144*a*, 144*b* and 144*c* are connected to respective inflation syringes 114*a*, 114*b* and 114*c* which have respective inflation syringe plungers 98*a*, 98*b*, and 98*c*. In this alternate embodiment, evacuation syringe 112 is mounted behind pressure gauge 90. As before, the distal end of conduit 82 is connected to sealing system 60. Sealing system 60 is comprised of compression sealing mechanism 200 and crimping mechanism 66.

Figure 4:
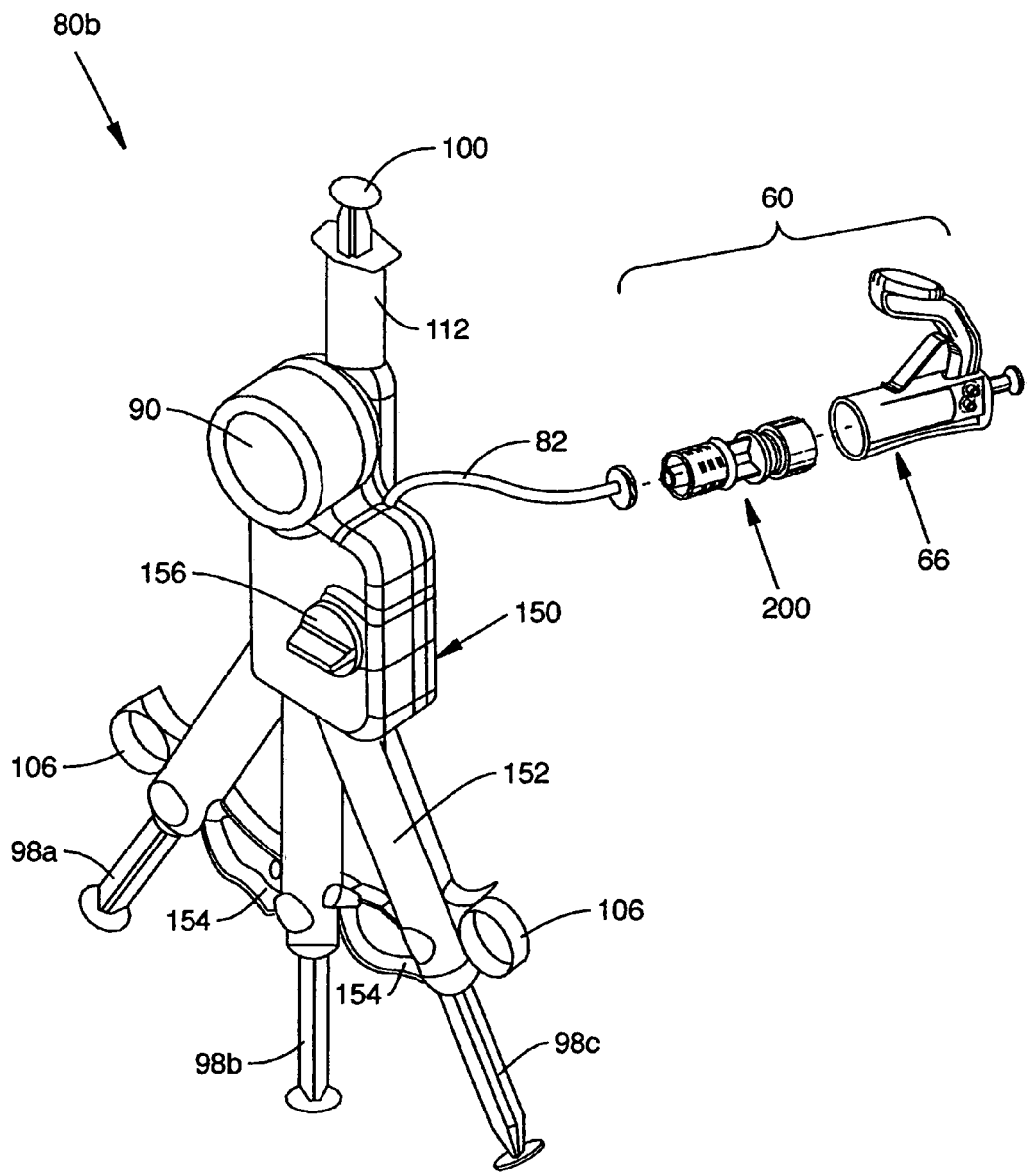
FIG. 4 is a perspective view of another alternate embodiment of a gas inflation/evacuation system and sealing system of the present invention.

FIG. 4 shows an alternate gas inflation/evacuation system 80*b* that is similar to the gas inflation/evacuation system 80*a* shown in FIG. 3 except that the components are arranged in a common housing 150. Common housing 150 has internal sealed channels that fluidly interconnect via valve arrangement 108 to evacuation syringe 112 and to inflation syringes 114*a*, 114*b* and 114*c* and pressure gauge 90. Common housing 150 has structure 152 that defines chambers for the three inflation syringes 114*a*, 114*b* and 114*c*. Common housing 150 also includes structure defining external fingergrips 106 and internal fingergrips 154 between adjacent portions of structure 152. Common housing 150 also contains structure for integrating evacuation syringe 112 and pressure gauge 90 as part of the common housing 150. An external knob 156 connects to the valve arrangement 108 for operating the valve arrangement 108.

The alternate embodiments shown in FIGS. 3 and 4 allow for effective pressurization of occlusive balloon 32 at less than 2 atmospheres while reducing the total volume of gas that might be introduced into a patient in the event of a leak in the guidewire occlusion system 20. Depending upon the desired inflation pressure and the total number of inflation cycles, the total amount of pressurized gas in a single inflation syringe such as 88 in FIGS. 1 and 2 can be significant. If a leak were to occur, the entire contents of a single inflation syringe would be susceptible to that leak. By using a separate inflation syringe 114a, 114b, 114c for each inflation in the alternate embodiments shown in FIGS. 3 and 4, these alternate embodiments provide a simple way of decreasing the total amount of pressurized gas that might be introduced into a patient in the event of a leak in the guidewire occlusion system 20.

Figure 5:
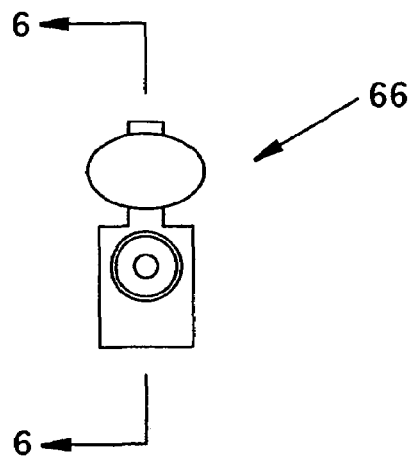
FIG. 5 is an end view of a crimping mechanism.
Figure 6:
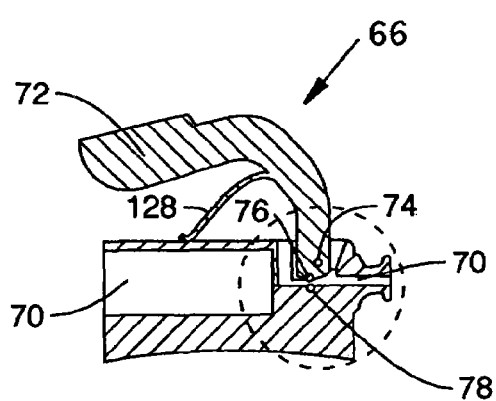
FIG. 6 is a sectional view taken along the line 6-6 of FIG. 5.
Figure 7:
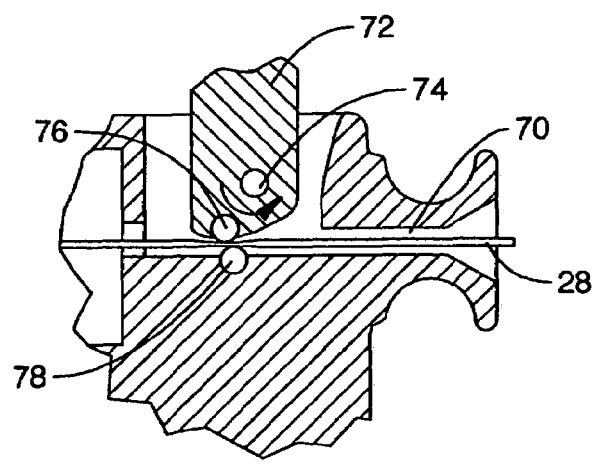
FIG. 7 is a magnification of the portion of FIG. 6 indicated by the dashed circle.

Details of the crimping mechanism 66 are shown in FIGS. 5-7, and details of the compression sealing mechanism 200 as well as alternate compression sealing mechanisms 250 and 300 are shown in FIGS. 8-18.

FIG. 5 is an end view of the crimping mechanism 66; FIG. 6 is a sectional view taken along the line 6-6 of FIG. 5; and FIG. 7 is a magnification of the portion of FIG. 6 indicated by the dashed circle. As shown in these figures, the crimping mechanism 66 comprises a handle 72 equipped with a springlike handle return 128 that actuates a pivotable cam arrangement 74 that crimps and then severs the extended sealable section 28 between a pair of rollers 76, 78 by mechanically flattening and pinching the extended sealable section 28 to the point of breaking. Preferably, crimping mechanism 66 and compression sealing mechanism 200 are arranged coaxially with each other along a straight portion of passageway 70. When the proximal end 36 of guidewire 24 is inserted into first aperture 62 until the proximal end 36 engages the compression sealing mechanism 200, the extended sealable section 28 is properly positioned relative to the crimping mechanism 66. By having sufficient length of the extended sealable section 28, the extended sealable section 28 can be coupled to the gas inflation/evacuation system 80 via the crimping mechanism 66 and the compression sealing mechanism 200 multiple times, allowing the occlusive balloon 32 to be inflated and deflated multiple times.

Figure 8:
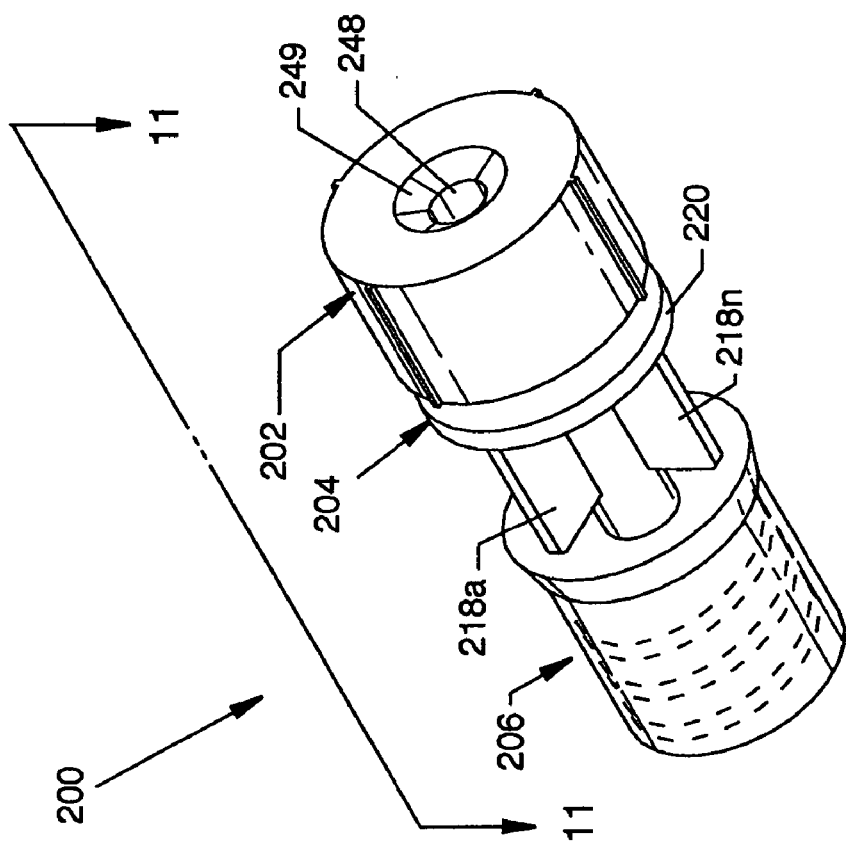
FIG. 8 is an isometric view of a compression sealing mechanism in accordance with the present invention in assembled condition.

FIG. 8 is an isometric view of the compression sealing mechanism 200 in assembled condition. Immediately visible components in the view include a sealing cap 202, a configured one-piece sealing gland 204, and a fluid connector 206.

Figure 9:
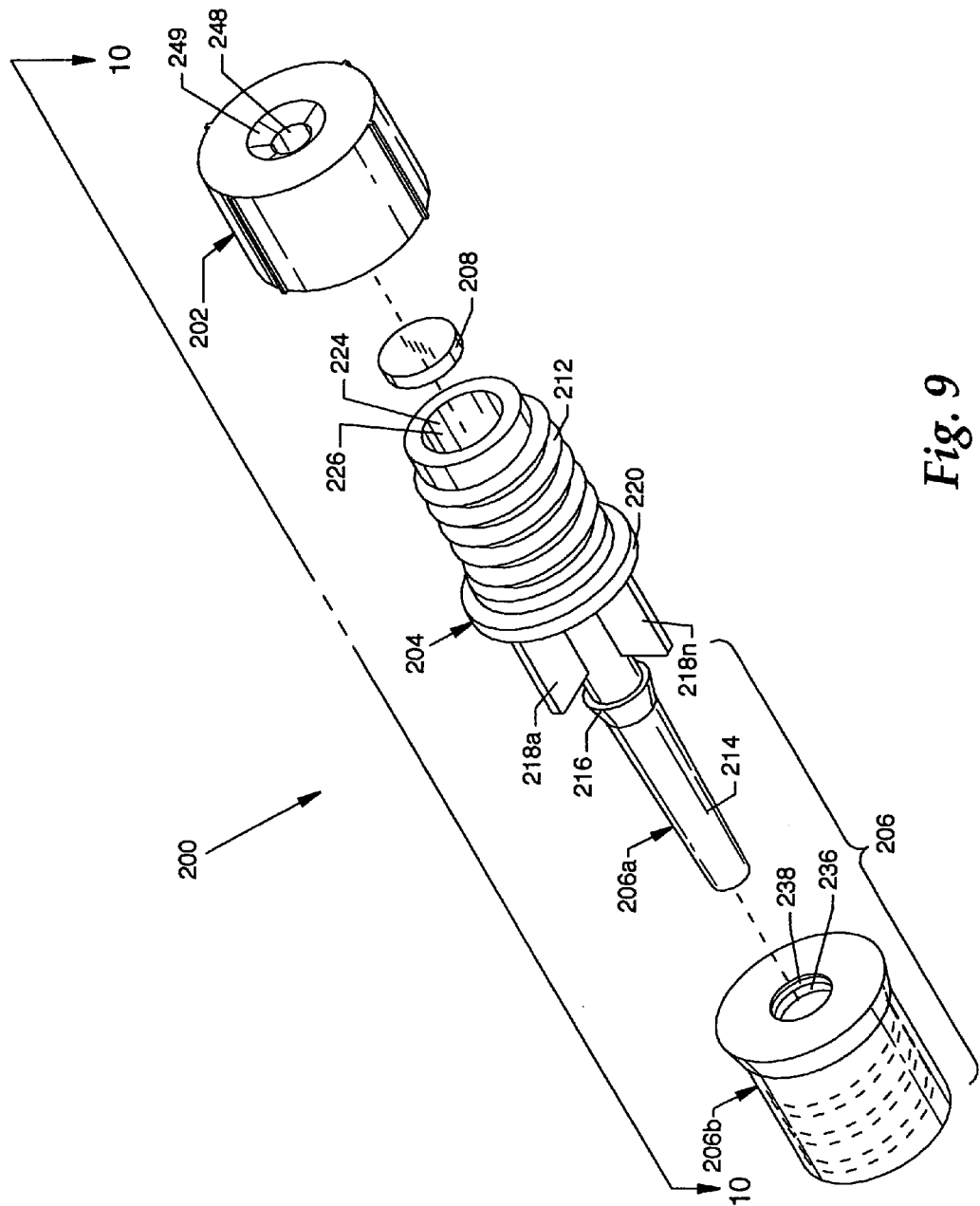
FIG. 9 is an exploded view of the compression sealing mechanism shown in FIG. 8.

FIG. 9 is an exploded view of the compression sealing mechanism 200 shown in FIG. 8. FIG. 9, in addition to showing the sealing cap 202, the one-piece sealing gland 204, and the fluid connector 206, shows a seal 208 constructed of a resilient material, preferably silicone. The seal 208 is imperforate, axially compressible and sealingly radially expandable, and is shaped as a disc having two substantially flat faces substantially parallel to each other and separated by a thickness. The sealing gland 204 serves as a mount for the sealing cap 202 and together with the sealing cap 202 constitutes a compressing apparatus for compressing the seal 208. Sealing gland 204 also serves as a mount for the fluid connector 206. Fluid connector 206 is illustrated as a male Luer connector with a Luer taper component 206a, which forms a fluid seal with the conduit 82 (see FIG. 12), and a threaded locking component 206b, which provides a secure mechanical attachment to the conduit 82. One end of the sealing gland 204 includes external threads 212 for receiving and mounting the sealing cap 202. Located along the longitudinal axis of the sealing gland 204 at the end thereof opposite to the external threads 212 is a connector tube 214 which forms a portion of the Luer taper component 206a and which has an annular ramp 216 over which the threaded locking component 206b is mounted by snap engagement and by which the threaded locking component 206b is captured and rotatably retained upon the connector tube 214 distal to the annular ramp 216 and adjacent to a plurality of support struts 218a-218n extending along a portion of the connector tube 214 and terminating at an annular ridge 220, which is shown to be continuous, but which could be spaced segments, for manual grasping.

Figure 10:
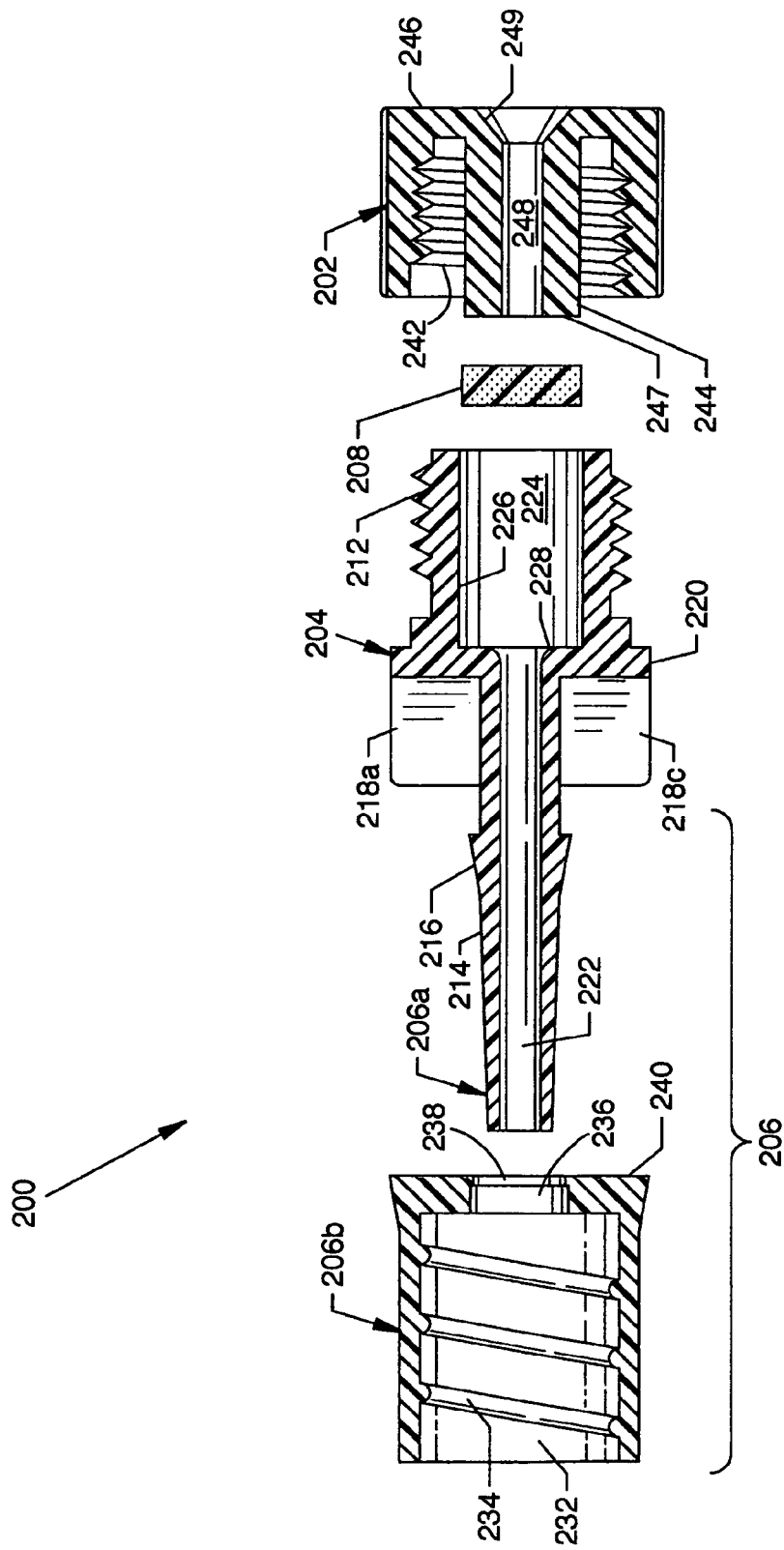
FIG. 10 is an exploded cross section view taken along line 10-10 of FIG. 9.

FIG. 10 is an exploded cross section view taken along line 10-10 of FIG. 9. Shown in particular is a distally located cavity 224 extending along and about the longitudinal axis of the sealing gland 204. The cavity 224 includes a circular peripheral wall 226 intersecting a surface in the form of a sealing seat 228 which is planar in nature. A passageway 222 extends partially along and about the longitudinal axis of the sealing gland 204 and within the connector tube 214 in communication with the cavity 224. The threaded locking component 206b of the fluid connector 206 includes an interior cavity 232 which is tubular and includes a raised threaded surface 234 for accommodation and fixation to desired appliances. A hole 236 having an annular ridge 238 is located in the end wall 240 of the threaded locking component 206b. The annular ridge 238 snappingly engages over and about the annular ramp 216 of the connector tube 214 to rotatably retain the threaded locking component 206b upon the connector tube 214, as previously described. The sealing cap 202 includes internal threads 242 suitable for threadingly engaging the external threads 212 of the sealing gland 204. A tubular extension 244 extends proximally from the end wall 246 of the sealing cap 202 and terminates in an annular planar sealing face 247. A passageway 248 having a distally located annular bevel 249 extends from the end wall 246 through the tubular extension 244 and intersects the annular planar sealing face 247.

Figure 11:
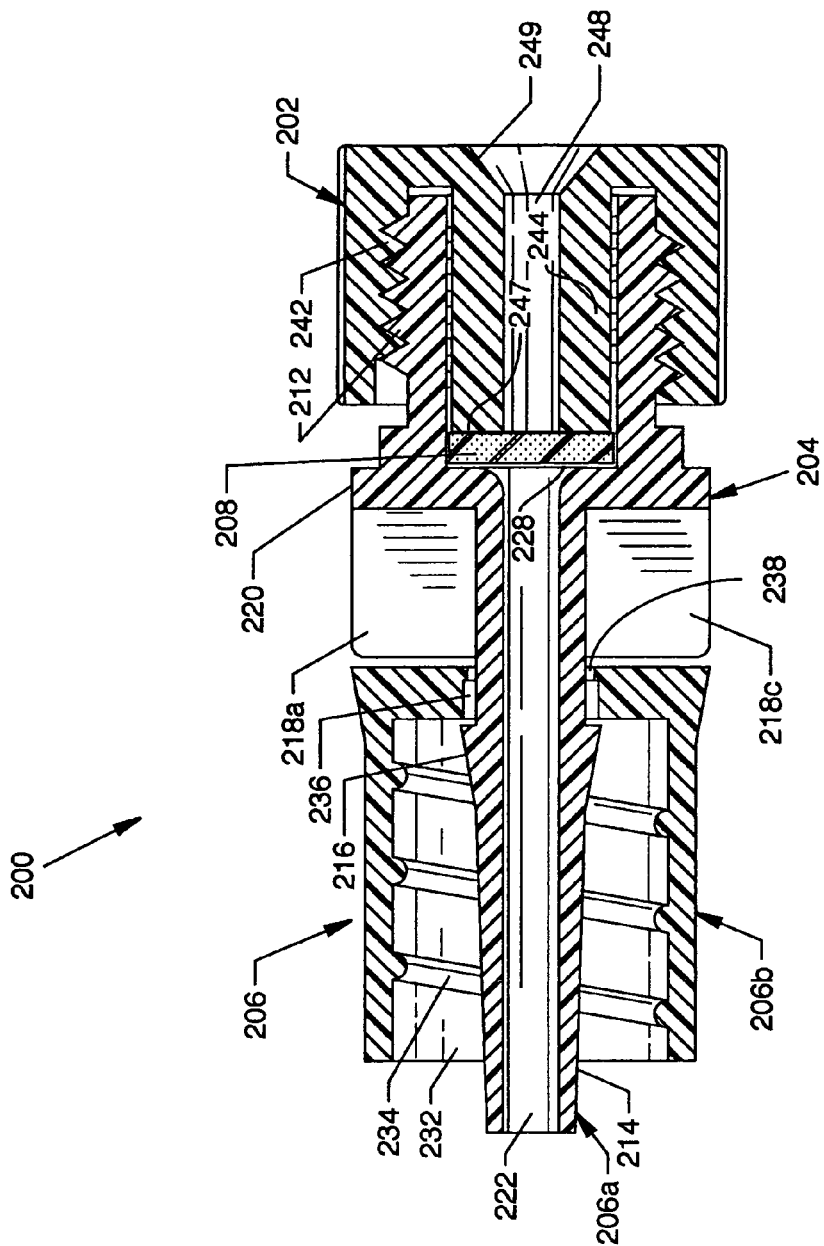
FIG. 11 is a cross section view of the assembled compression sealing mechanism taken along line 11-11 of FIG. 8.
Figure 12:
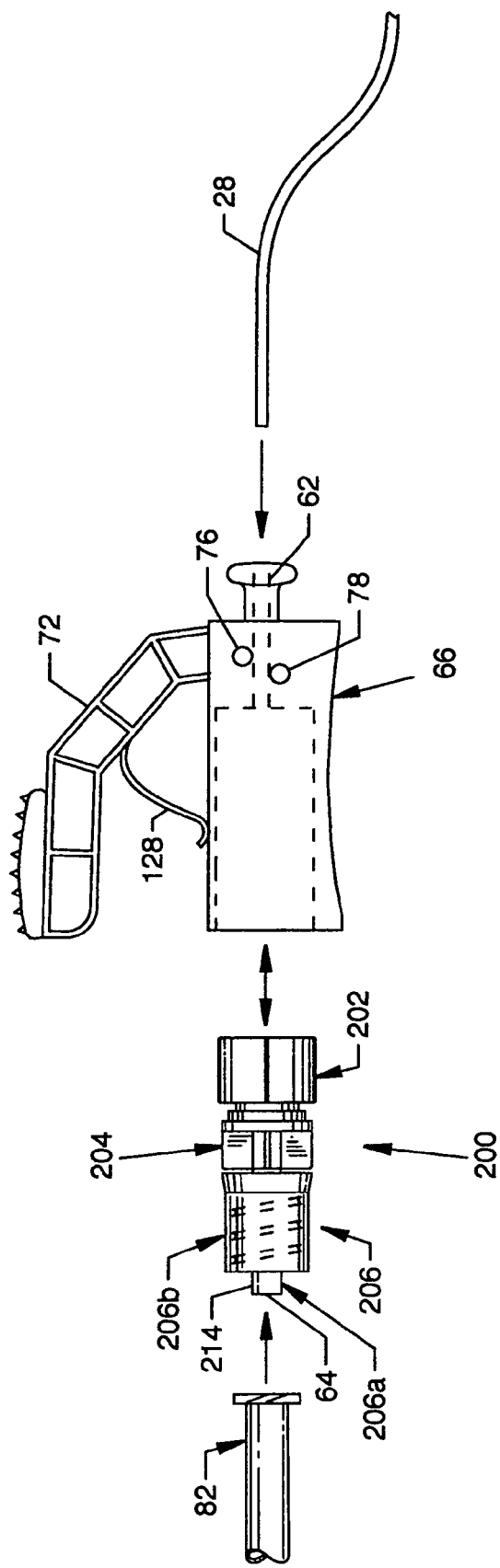
FIG. 12 shows the compression sealing mechanism in association with components of a guidewire occlusion system.

FIG. 11 is a cross section view of the assembled compression sealing mechanism 200 taken along line 11-11 of FIG. 8, and FIG. 12 depicts the compression sealing mechanism 200 in association with crimping mechanism 66 and other components of the guidewire occlusion system. In use, the seal 208 is aligned in the cavity 224 preferably in initial contact with the sealing seat 228 followed by threaded engagement of the sealing cap 202 to the sealing gland 204 to capture the seal 208. A guidewire, catheter, or other like elongated element can then be introduced and guided by the annular bevel 249 into the passageway 248 of the sealing cap 202, and thence pushed through the seal 208 and into the passageway 222 of the connector tube 214. The guidewire, catheter, or other like elongated element substantially maintains a coaxial relationship to the annular bevel 249, the passageway 248, the seal 208, the cavity 224 and the passageway 222, the annular ridge 238, the hole 236, and the interior cavity 232 of the threaded locking component 206b, all of which have a mutual coaxial relationship along a central longitudinal axis. The internal threads 242 of the sealing cap 202 threadingly engage the external threads 212 of the sealing gland 204, and the sealing cap 202 is ratably advanced with respect to the sealing gland 204 to bring the annular sealing face 247 of the tubular extension 244 into intimate contact with the seal 208. Such advancing rotation causes the sealing face 247 of the sealing cap 202 to forcibly engage the seal 208 to compress the seal 208 between the sealing face 247 of the sealing cap 202 and the sealing seat 228 of the sealing gland 204 to cause inwardly directed closure movement of the seal 208 and to expand the periphery of the seal 208 radially and outwardly, thereby providing a seal against a guidewire, catheter or other like elongated element and against the circular peripheral wall 226 of the sealing gland 204, respectively. The compression sealing mechanism 200 reversibly lockably fits into the crimping mechanism 66. The fluid connector 206 of the compression sealing mechanism 200 receives the conduit 82, which is connectable to a gas inflation/evacuation system. The guidewire assembly extended sealable section 28 is passed through the first aperture 62, passed through the crimping mechanism 66, passed through the seal 208, and extended into the passageway 222 of the connector tube 214. The seal 208 seals around and about the extended sealable section 28. After crimping, the extended sealable section 28 is severed or otherwise broken off distal to the compression sealing mechanism and a remaining portion of the extended sealable section 28 subsequently may be reinserted through the seal 208. The breaking off and reinsertion process may be repeated as necessary.

Figure 13:
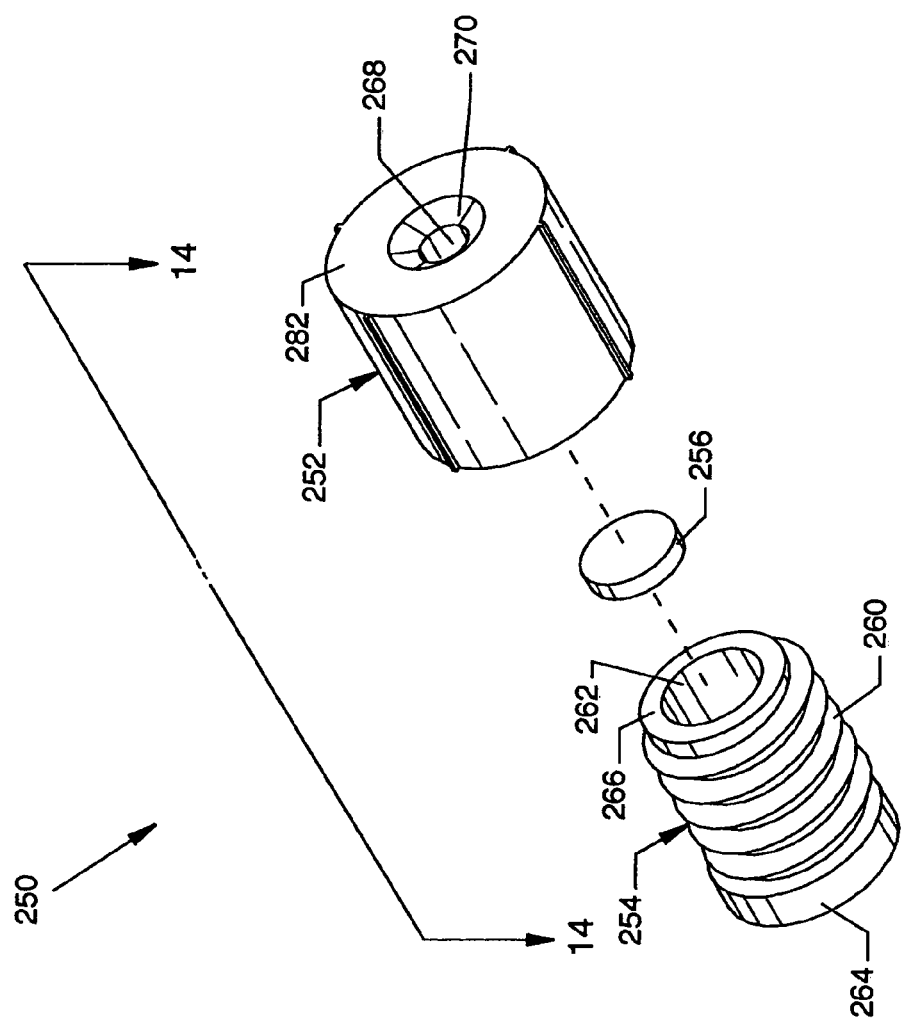
FIG. 13 is an exploded view of an alternate compression sealing mechanism.

FIG. 13 is an exploded view of an alternate embodiment compression sealing mechanism designated 250. Immediately visible components and other features shown in the view include a sealing cap 252, a configured one-piece sealing gland 254, and a seal 256, such seal 256 being similar to seal 208 in construction, composition and qualities. The sealing gland 254 includes a central cavity 262 for accommodation of seal 256, and also includes a continuous annular ridge 264 suitable for manual grasping and handling. Alternatively, the continuous annular ridge 264 could be replaced by spaced ridges for facilitation of manual grasping. The sealing gland 254 also serves as a mount for the sealing cap 252 and together with the sealing cap 252 constitutes compressing apparatus for compressing the seal 256. The sealing gland 254 includes external threads 260 for receiving and for accommodation of the sealing cap 252. An annular surface 266 at one end of the cavity 262 adjacent to the external threads 260 is also shown. The sealing cap 252 includes a passageway 268 having an annular bevel 270 opening from an end wall 282.

Figure 14:
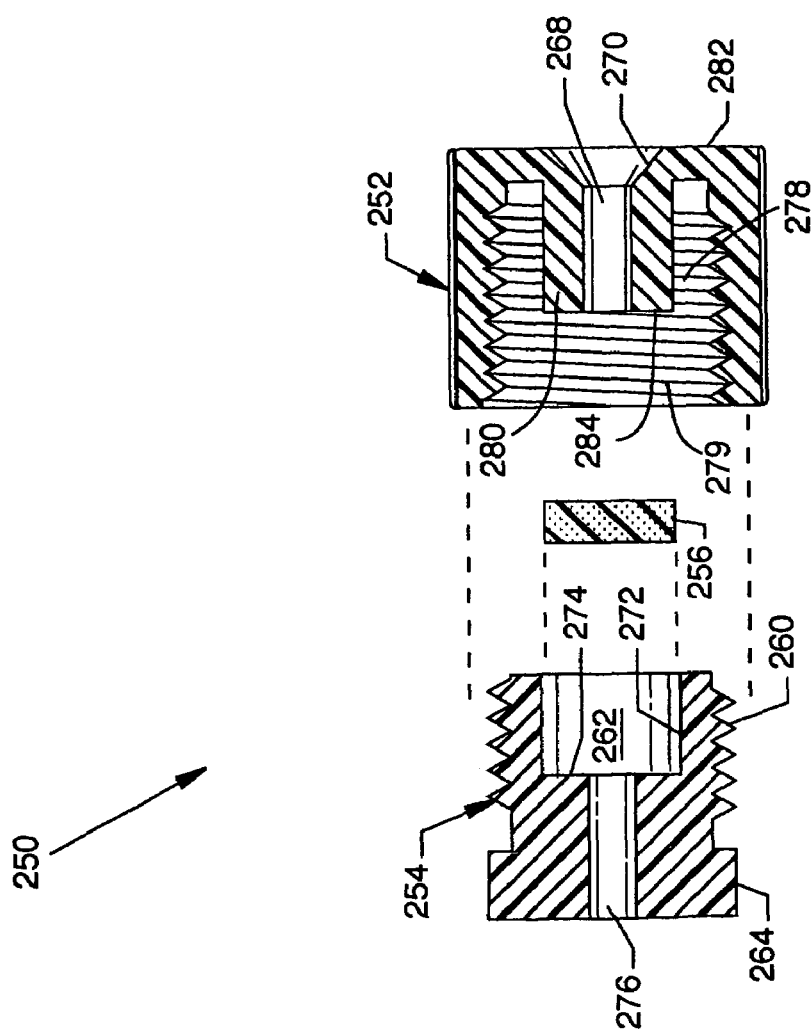
FIG. 14 is an exploded cross section view taken along line 14-14 of FIG. 13.

FIG. 14 is an exploded cross section view taken along line 14-14 of FIG. 13. Shown in particular is the distally located cavity 262, which is cylindrical in shape, extends along and about the longitudinal axis of the sealing gland 254, and includes a circular peripheral wall 272 intersecting a sealing seat 274 which is planar in nature. A passageway 276 in communication with the cavity 262 extends partially along and about the longitudinal axis of the sealing gland 254, the general location of which is in close proximity to the annular ridge 264. The sealing cap 252 includes internal threads 278 suitable for threadingly engaging the external threads 260 of the sealing gland 254. A tubular extension 280, which includes the passageway 268, extends proximally from the end wall 282 of the sealing cap 252 partially along a cavity 279 defined by the internal threads 278 and the end wall 282 of the sealing cap 252 to include a proximally located annular planar sealing face 284 at one end.

Figure 15:
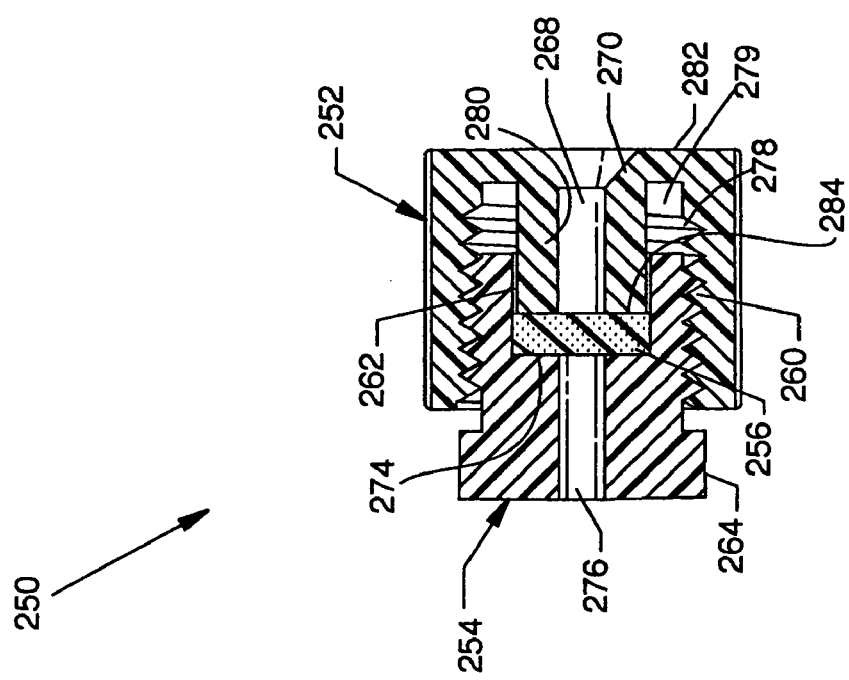
FIG. 15 is a cross section view of the compression sealing mechanism of FIG. 13 in assembled condition.

FIG. 15 is a cross section view of the assembled compression sealing mechanism 250. In use, the seal 256 is aligned in the cavity 262 preferably in initial contact with the sealing seal 274 at one end of the cavity 262 followed by threaded engagement of the sealing cap 252 to the sealing gland 254 to capture the seal 256. A guidewire, catheter, or other like elongated element can then be introduced and guided by the annular bevel 270 into the passageway 268 of the sealing cap 252 and through the seal 256 and thence into the passageway 276 of the sealing gland 254. The guidewire, catheter, or other like elongated element substantially maintains a coaxial relationship to the annular bevel 270, the passageway 268, the seal 256, the cavity 262, and the passageway 276, all of which have mutual coaxial relationship along a central longitudinal axis. The internal threads 278 of the sealing cap 252 threadingly engage the external threads 260 of the sealing gland 254, whereby the sealing cap 252 can be rotatably advanced with respect to the sealing gland 254 to bring the annular planar sealing face 284 of the tubular extension 280 into intimate contact with the seal 256. Such advancing rotation causes the sealing face 284 of the sealing cap 252 to forcibly engage the seal 256 to compress the seal 256 between the sealing face 284 of the sealing cap 252 and the sealing seat 274 of the sealing gland 254 to expand the periphery of the seal 256 radially and outwardly, thereby providing a seal against a guidewire, catheter, or other like elongated element and against the circular peripheral wall 272 of the sealing gland 254, respectively.

Figure 16:
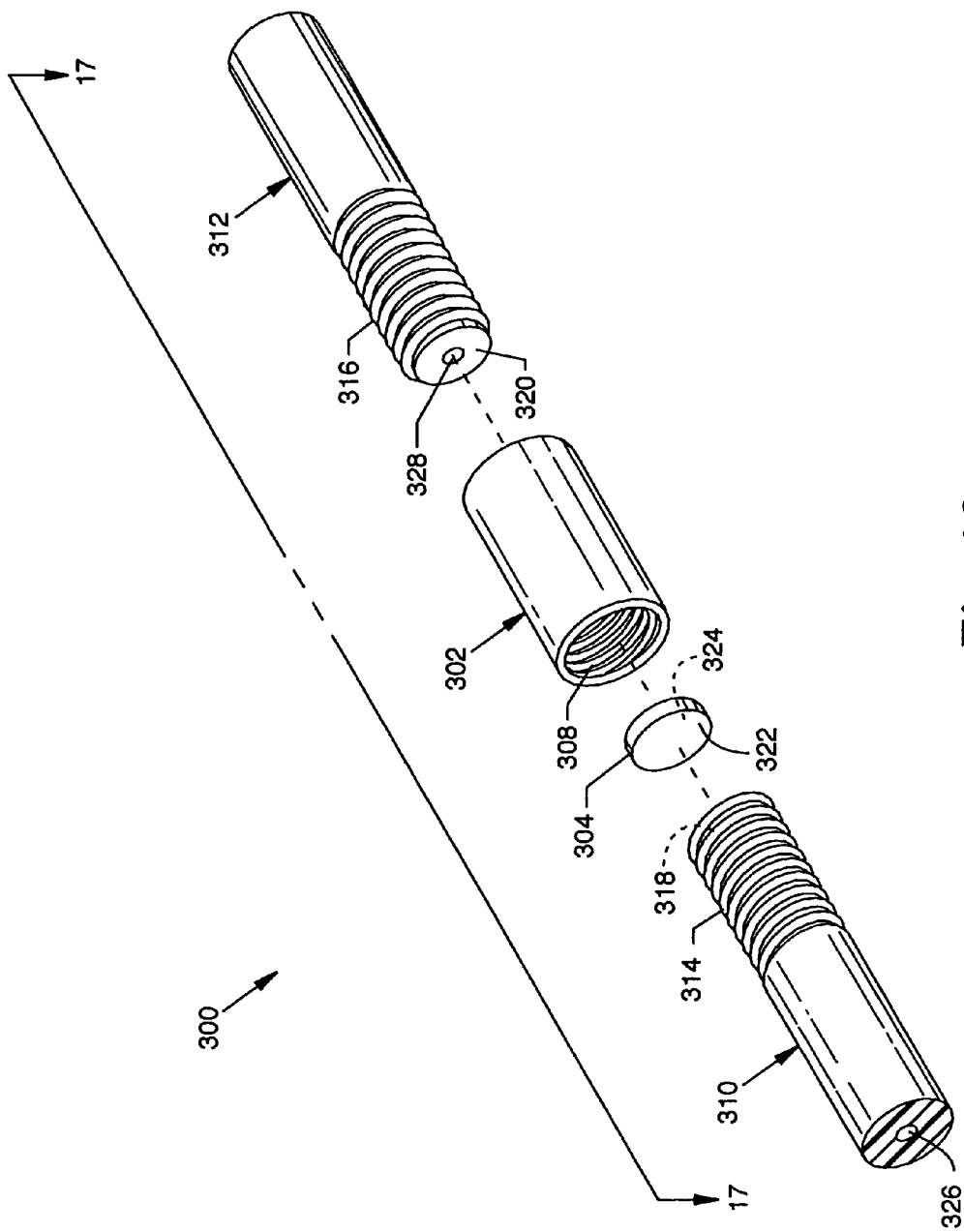
FIG. 16 is an exploded isometric view of another alternate compression sealing mechanism.
Figure 17:
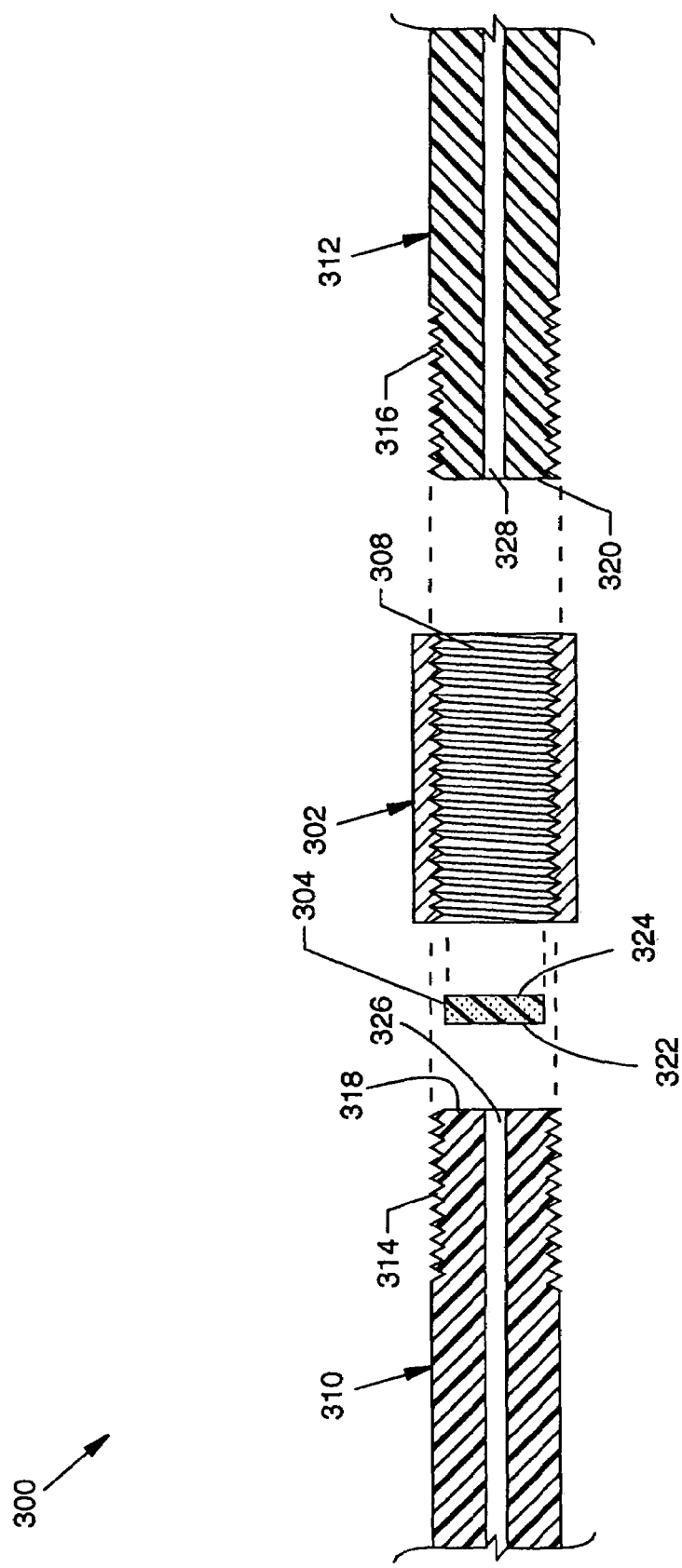
FIG. 17 is an exploded cross section view taken along line 17-17 of FIG. 16; and, FIG. 18 is a cross section view of the compression sealing mechanism of FIG. 16 in assembled condition.
Figure 18:
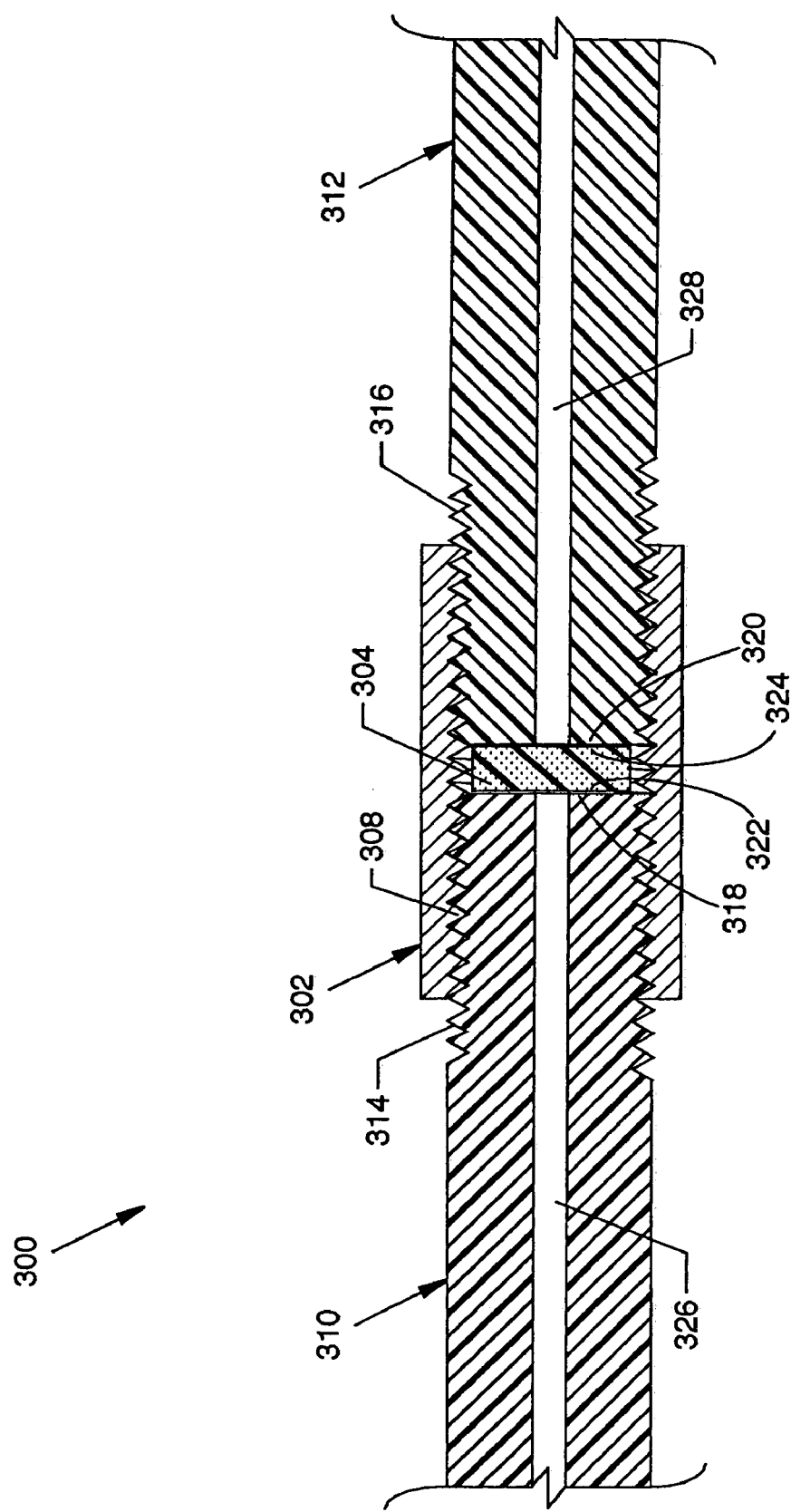

FIGS. 16-18 are exploded isometric, exploded cross section, and assembled cross section views respectively, illustrating another alternate compression sealing mechanism, therein designated 300. The compression sealing mechanism 300 utilizes a central sleeve 302 of metal, plastic, or other suitable material which houses a seal 304, such seal 304 preferably being similar to seal 208 in construction, composition, qualities and attributes. The central sleeve 302 is tubular in shape and includes interior threads 308 which can extend continuously from one end to the other, as shown, or can be provided only at the ends. Opposing tubes 310 and 312, each being part of the compression sealing mechanism 300 and which together constitute compressing apparatus, can be similar in construction, can be flexible, and can include exterior threads 314 and 316, all as shown. The exterior threads 314 and 316 of tubes 310 and 312 are threadingly accommodated by the interior threads 308 of the central sleeve 302. The near ends of the opposing tubes 310 and 312 include flat sealing faces 318 and 320 which forcibly mate and seal against opposing planar sides 322 and 324, respectively, of the seal 304 by threadingly advancing the exterior threads 314 and 316 of the tubes 310 and 312 along the interior threads 308 of the central sleeve 302. A lumen 326 extending along tube 310 intersects the flat sealing face 318 of tube 310 and, correspondingly, a lumen 328 extending along the tube 312 intersects the flat sealing face 320 of tube 312. The opposing tubes 310 and 312 are representative of any tubular type devices which may require sealable coupling through which a guidewire, catheter, or elongated element may be accommodated and take advantage of the sealed structure of the compression sealing mechanism 300. Preferably, the opposing tubes 310 and 312 are of similar shape and size; however, the configuration of each tube 310 and 312 may vary slightly, such as the diameter of the lumen 326 in the tube 310 and the lumen 328 in the tube 312, so long as the sealing integrity is maintained.

Also, the use of threaded surfaces could be eliminated, whereby the exterior threads 314 and 316 of tubes 310 and 312 and the interior threads 308 of the central sleeve 302 could be replaced by smooth surfaces, such smooth surfaces being straight-walled or of a tapered nature. When using straight-walled surfaces, an adhesive could be utilized to join the respective components. When using tapered surfaces, frictional engagement alone or adhesive in concert with frictional engagement could be utilized to join the components.

In use, the exterior threads of one tube, such as the exterior threads 314 of tube 310, are made to engage the interior threads 308 of the sleeve 302. The seal 304 is then inserted into the other end of the sleeve 302 followed by engagement of the exterior threads 316 of the remaining tube 312, advancing the exterior threads 316 of the tube 312 until the planar sides 322 and 324 of the seal 304 are intimately and forcibly contacted by the flat sealing faces 318 and 320 of the tubes 310 and 312. Such contact communicatingly seals the lumen 326 of tube 310 from the lumen 328 of the tube 312 by the intermediately located seal 304. A guidewire, catheter, or such similar elongated element can be introduced into one of the lumens, such as lumen 328 of the tube 312, and urged further along and through the seal 304 and into the remaining lumen 326 of the tube 310. Such a path through the compressed seal 304 offers a sealed contact about the guidewire, catheter, or like elongated element. The degree of compressional mutual sealing of the seal 304 about the guidewire, catheter, or like elongated element is increased by rotational advancement of the ends of the tubes 310 and 312 towards each other within the sleeve 302.

In each of the compression sealing mechanisms 200, 250 and 300 the material of the seal is resilient and a compressive force applied to the seal is transmitted through the seal to force the material of the seal to close around elements that penetrate the material. Resilient refers to a material property that includes flexible, compressible, recoverable, and elastic materials. Such materials transmit an applied compressive force into the interior of the seal so that the compressive force helps the seal to close around a penetrating element so that a seal is effective. Examples of resilient materials are silastics, rubbers, fluoroelastomers, synthetic rubbers, and many types of urethanes. The resilient nature of the material can be adjusted for various applications. For example, the material may be made less resilient to provide a stronger, more durable, seal, or made more resilient to ease the passage of a tube or other elongated element through the material. Similarly, the thickness of the material may be adjusted, with thicker materials providing more durable seals and thinner materials easing the passage of elements through the seal.

For example, the compression sealing mechanism 200 depicted in FIGS. 8-11 was assembled with silicone seals having diameters of about 0.25 inch and thicknesses ranging from about 0.030 inches to about 0.08 inch. The seals were penetrated with a plurality of 0.015-inch diameter tubes and were pressure tested with about 80 psi of gas. The 0.030 inch thick seal tended to leak when moved. Thicker seals were more effective in preventing leakage, with a thickness of more than about 0.060 being very effective. A thickness of about 0.075±0.005 inch was about optimal when tubes of about 0.015 inch in diameter were used. The resilient seal was shown to seal around a plurality of 0.015-inch diameter sealed tubes, including as many as six tubes.

MODE OF OPERATION

In practice, medical personnel gain entry to the vessel lumen prior to use of the guidewire occlusion system 20. Once entry to the vessel lumen is gained, the distal portion 26 of guidewire 24 is inserted into the vessel lumen, and occlusive balloon 32 is inserted to a point distal to the vessel occlusion. Then, when employing the gas inflation/evacuation system 80 of FIGS. 1 and 2, the extended sealable section 28 of guidewire 24 is inserted into first aperture 62 and connected to the inflation/evacuation system 80 via crimping mechanism 66 and compression sealing mechanism 200 which are connected to conduit 82 at second aperture 64. When this is done the proximal end of the extended sealable section 28 will have been pushed through the seal 208. Next, valve arrangement 84 is set for evacuation; evacuation syringe plunger 92 of evacuation syringe 86 is slidably withdrawn removing any air from guidewire assembly 22; valve arrangement 84 is then set for inflation; and inflation syringe plunger 94 of inflation syringe 88 is slidably advanced inserting a volume of an inert gas into guidewire assembly 22. The inert gas inflates occlusive balloon 32 as shown in FIG. 2. During inflation, the medical personnel monitor pressure gauge 90 to ensure that the inflation pressure does not exceed the burst rating of the occlusive balloon 32 and to gauge the relative size of the occlusive balloon 32 as it is inflated. Following inflation of occlusive balloon 32, crimping mechanism 66 is employed to crimp the extended sealable section 28, thereby sealing the guidewire assembly 22 to maintain the occlusive balloon 32 in an inflated state. To operate the crimping mechanism 66, handle 72 of the crimping mechanism 66 is depressed causing roller 76 and roller 78 to crimp and preferably sever the extended sealable section 28 of guidewire 24. Severing of the extended sealable section 28 serves as an immediate verification of the creation of an effective seal. Extended sealable section 28 distal to the severed location can be completely removed from the sealing system 60 allowing the occlusive balloon 32 to remain inflated while occlusive substance treatment occurs. When the extended sealable section 28 is removed from first aperture 62, the guidewire 24 is free of mechanical or other obstructions and can function as a conventional guidewire. When the medical personnel decide to deflate the occlusive balloon 32, the extended sealable section 28 is cut distal to the existing crimp using a medical scissors, resulting in the immediate deflation of the occlusive balloon 32. If occlusive treatment is complete, guidewire assembly 22 can be removed from the vessel lumen. If additional treatment is required, the remaining intact portion of the extended sealable section 28 can be reattached to sealing system 60 through first aperture 62 and again connected via crimping mechanism 66 and compression sealing mechanism 200 to conduit 82. The evacuation/inflation process can then be repeated. Each time the extended sealable section 28 is severed, the fragment thereof proximal to the location whereat it is severed remains extending through the seal 208. At least six severed fragments can be held by the seal 208 before replacement is necessary.

The foregoing mode of operation was explained in reference to the gas inflation/evacuation system 80 and the sealing system 60 involving the compression sealing mechanism 200. It is to be understood that the same procedural steps followed when employing the gas inflation/evacuation system 80 and the compression sealing mechanism 200 are performed when utilizing the alternate gas inflation/evacuation system 80a or 80b and the alternate compression sealing mechanism 250 or 350.

It will be understood that a crimping handle 72 may also be provided with a separate severing arrangement to sever the extended sealable section 28. Alternatively, extended sealable section 28 may be scored or otherwise weakened in selected locations to assist in crimping to enable breaking by repeated bending back and forth at one of the scored locations. In another embodiment, the extended sealable section 28 could be fabricated of a brittle metal that aids in severing or otherwise breaking off the extended sealable section 28.

In a preferred embodiment of the present invention, the guidewire 24 is utilized as the guidewire for an atherectomy or thrombectomy procedure of the type described in U.S. Pat. Nos. 5,370,609 or 5,496,267, the disclosures of both of which are hereby incorporated by reference. In each of these procedures, the guidewire assembly 22 is introduced into the patient, the occlusive balloon 32 is inflated, and then the atherectomy or thrombectomy catheter arrangement is slid over the proximal end 36 of the guidewire 24 and advanced until it is proximate and proximal to the location of the occlusive balloon. The procedure is performed for a time period consistent with the desired maximum length for blockage of the particular vessel at which time the extended sealable section 28 may be severed to deflate the occlusive balloon 32, thereby reestablishing blood flow within the vessel. Depending upon the nature of the procedure, the catheter arrangement may be removed from the vessel or left in place. Preferably, an evacuation of any plaque material or other debris dislodged by the therapy is accomplished before deflation of the occlusive balloon 32. The occlusive balloon 32 is reinflated prior to reinitiation of the procedure.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention. Also, various modifications can be made to the present invention without departing from the apparent scope thereof.

Various modifications can be made to the present invention without departing from the apparent scope thereof.

It is claimed:

1. A gas inflation/evacuation system and sealing system removably connectable to a proximal portion of a guidewire assembly having a guidewire that defines a lumen, comprising:
   a. the gas inflation/evacuation system and sealing system adapted to removably attach to a guidewire assembly having
      (1) a guidewire with a lumen along the length thereof;
      (2) an occlusion balloon in fluid communication with the lumen which thereby can be inflated and deflated via the lumen;
      (3) the guidewire having a crimpable portion which is permanently deformable to occlude the lumen thereby maintaining the balloon in an inflated state;
   b. the gas inflation/evacuation system and sealing system adapted to removably attach to a crimping mechanism having
      (1) pinch points adapted to crimp the guidewire to permanently deform the guidewire to occlude the lumen thereby maintaining the balloon in an inflated state after removal of the crimping mechanism;
   c. a first syringe system for selectively evacuating the lumen;
   d. a second syringe system for selectively introducing a biocompatible gas into the lumen to inflate the occlusion balloon that is in fluid communication with the lumen and that is located proximate a distal end of the guidewire assembly;
   e. a compression sealing mechanism removably connectable to the proximal portion of the guidewire that comprises:
      (1) a resilient seal for receiving and sealing around the proximal portion of the guidewire;
      (2) a compressing apparatus for compressing the resilient seal, the compressing apparatus comprising a sealing cap and a sealing gland, the sealing cap having threads and the sealing gland having threads to engage the threads of the sealing cap; and,
   f. wherein the compression sealing mechanism is adapted to seal around the proximal portion of the guidewire while the crimping mechanism is used to permanently deform the guidewire to occlude the lumen thereby maintaining the balloon in an inflated state.

2. The system of claim 1, wherein the resilient seal, when compressed, automatically seals around elements that penetrate the resilient seal without need for adjustment of the compressing apparatus.

3. The system of claim 1, wherein the sealing gland includes a planar sealing seat and the sealing cap includes a planar sealing face that is substantially parallel to the planar sealing seat of the sealing gland so that, when the planar sealing face of the sealing cap is in contact with the resilient seal, the planar sealing face of the sealing cap transmits compressive force to the resilient seal to force the resilient seal against the planar sealing seat of the sealing gland, thereby compressing the resilient seal.

4. The system of claim 1, wherein the resilient seal comprises an elastomeric polymer.

5. The system of claim 4, wherein the resilient seal comprises two substantially flat faces substantially parallel to each other and separated by a thickness.

6. The system of claim 5, wherein the thickness ranges from about 0.030 inch to about 0.200 inch.

7. The system of claim 4, wherein the elastomeric polymer is silicone.

8. The system of claim 1, wherein the resilient seal is shaped as a disc.

9. The system of claim 8, wherein the disc has a thickness that ranges from about 0.030 inch to about 0.080 inch.

10. The system of claim 1, wherein the gas inflation/evacuation system and the sealing system constitute a hand-held apparatus, and wherein the sealing system includes a first aperture into which the proximal portion of the guidewire is selectively insertable and a second aperture to which the gas inflation/evacuation system is operably connected, there being an airtight passageway connecting the first aperture and the second aperture.

11. The system of claim 1, further comprising a crimping mechanism.

12. The system of claim 11, wherein the crimping mechanism comprises:
   a. a first roller and a second roller proximately spaced from the first roller for traversal of the proximal portion of the guidewire, the first roller being connected to a handle with a pivotable cam arrangement such that force on the handle causes the first roller to proportionately approach the second roller, a first threshold force on the handle causing sealing of the proximal portion of the guidewire, and a second threshold force on the handle causing severing of the proximal portion of the guidewire.

13. The system of claim 1, wherein said guidewire has an outer diameter of less than 0.040 inch.

14. The system of claim 1, wherein said guidewire has an outer diameter of less than 0.020 inch.

15. The system of claim 1, wherein the largest outer diameter of said guidewire is between approximately 0.010 inch and 0.018 inch.

* * * * *